US008648057B2

(12) United States Patent
Holzer et al.

(10) Patent No.: US 8,648,057 B2
(45) Date of Patent: Feb. 11, 2014

(54) PHARMACEUTICAL COMPOSITION FREE FROM DEXPANTHENOL, CALCIUM IONS, AND PHOSPHATE AND USE OF CALCIUM CHELATING AGENT AND OPHTHALMOLOGICALLY COMPATIBLE VISCOSITY REGULATOR

(75) Inventors: Frank Holzer, St. Ingbert (DE); Dorothea Gross, St. Ingbert (DE)

(73) Assignee: Ursapharm Arzneimittel GmbH & Co. KG, Saarbrucken (DE)

( * ) Notice: Subject to any disclaimer, the term of this patent is extended or adjusted under 35 U.S.C. 154(b) by 810 days.

(21) Appl. No.: 12/084,803

(22) PCT Filed: Nov. 17, 2006

(86) PCT No.: PCT/EP2006/011053
§ 371 (c)(1),
(2), (4) Date: Jul. 10, 2008

(87) PCT Pub. No.: WO2007/057201
PCT Pub. Date: May 24, 2007

(65) Prior Publication Data
US 2009/0111770 A1 Apr. 30, 2009

(30) Foreign Application Priority Data
Nov. 17, 2005 (DE) .......................... 10 2005 055 275

(51) Int. Cl.
*A61K 31/728* (2006.01)
*C08B 37/00* (2006.01)
*C08B 37/08* (2006.01)

(52) U.S. Cl.
CPC ........... *A61K 31/728* (2013.01); *C08B 37/0072* (2013.01)
USPC .......................................... 514/54; 536/55.1

(58) Field of Classification Search
None
See application file for complete search history.

(56) References Cited

U.S. PATENT DOCUMENTS

| 4,409,205 | A | | 10/1983 | Shively |
| 5,705,485 | A | * | 1/1998 | Cini et al. ...................... 514/8.2 |
| 6,271,216 | B1 | * | 8/2001 | Mello et al. ...................... 514/54 |
| 6,605,295 | B1 | * | 8/2003 | Bellmann et al. ............. 424/427 |
| 7,083,803 | B2 | * | 8/2006 | Peyman ........................ 424/422 |
| 2004/0057980 | A1 | | 3/2004 | Wagenaar |
| 2005/0043271 | A1 | * | 2/2005 | Gross et al. ...................... 514/54 |
| 2005/0164979 | A1 | * | 7/2005 | Gross et al. ...................... 514/54 |
| 2006/0106104 | A1 | * | 5/2006 | Vehige et al. .................. 514/546 |
| 2006/0211599 | A1 | | 9/2006 | Suzuki |

FOREIGN PATENT DOCUMENTS

| DE | 10161110 A1 | 6/2003 |
| DE | 60203691 T2 | 3/2006 |
| EP | 414373 A | 2/1991 |
| EP | 464727 A | 1/1992 |
| EP | 698388 A | 2/1996 |
| EP | 1556184 A1 | 8/2005 |
| EP | 1752158 A1 | 2/2007 |
| GB | 2160097 A | 12/1985 |
| JP | A-2-96515 | 4/1990 |
| JP | 07048262 | 2/1995 |
| JP | 2003002837 | 1/2003 |
| JP | 2003206241 A | 7/2003 |
| JP | 2003342197 | 12/2003 |
| JP | 2004059432 | 2/2004 |
| JP | 2005239622 | 9/2005 |
| WO | WO84/04681 | 12/1984 |
| WO | WO02/15828 | * 2/2002 .............. A61F 9/007 |

OTHER PUBLICATIONS

Merriam-Webster's Collegiate Dictionary, published 1998 by Merriam-Webster, Incorporated, p. 924.*
"Kollidon® 25" Downloaded from Signa-Aldrich.com, copyright 2011 Sigma-Aldrich Co. LLC.*
Brewitt et al., "Dry Eye Disease: The Scale of the Problem" Survey of Ophthalmology (2001) vol. 45 supplement 2 pp. S199-S202.*
Schoffling, The Comod® System, PTA Today, No. 12, pp. 1230-1232 (Dec. 1996).
Avisar, et al., Isr. J. Med. Sci., vol. 33, pp. 194-197(1997).
Aragona, et al., Br.J. Ophthalmology, vol. 86, pp. 181-184(2002).
Office Action dated Oct. 18, 2012 in corresponding Chinese Application No. 200680043135.X.
Office Action dated Nov. 2, 2012 in corresponding Canadian Patent Application No. 2630193.
Office Action dated Jun. 5, 2012, in corresponding Japanese Patent Application No. 2008-540522.

* cited by examiner

Primary Examiner — Eric S Olson
(74) Attorney, Agent, or Firm — Elliot M. Olstein; Raymond J. Lillie

(57) ABSTRACT

The invention relates to a pharmaceutical composition free from dexpanthenol, calcium ions and phosphate, comprising at least one calcium chelating agent and at least one opthalmologically compatible viscosity regulator and optionally one or more pharmaceutical excipients. The invention further relates to the use of a calcium chelating agent and an opthalmologically compatible viscosity regulator for the production of a phosphate-free pharmaceutical composition for the treatment and/or prevention of epithelial defects.

12 Claims, 2 Drawing Sheets

Carrying out the abrasion

Abrasion

Staining with fluorescein

Cornea at the beginning of the experiment

Cornea without sclerosis after dripping on phosphate-free eyedrops for 4 days

Cornea at the beginning of the experiment

Cornea with sclerosis after dripping on phosphate-containing eyedrops for 4 days Cornea at the beginning of the experiment Cornea with sclerosis after dripping on medium for 4 days

PHARMACEUTICAL COMPOSITION FREE FROM DEXPANTHENOL, CALCIUM IONS, AND PHOSPHATE AND USE OF CALCIUM CHELATING AGENT AND OPHTHALMOLOGICALLY COMPATIBLE VISCOSITY REGULATOR

The invention relates to a pharmaceutical composition free from dexpanthenol, calcium ions and phosphate. The invention further relates to the use of a calcium chelating agent and of an opthalmologically compatible viscosity regulator for the production of a pharmaceutical composition free from phosphate for the treatment and/or prevention of epithelial defects.

Viscosity regulators, in particular hyaluronic acid and hyaluronates, are used in wetting disorders of the eye, i.e. in the "dry eye" syndrome, which is also designated as the sicca syndrome or else as sicca symptomatology, and for the treatment of epithelial lesions which result from the wetting disorders.

In the "dry eye" syndrome these symptoms manifest themselves, inter alia, in burning, irritation, sensation of a grain of sand in the eye and blurred vision. These symptoms can be attributed to functional disorders of the lacrimal flow and/or of the tear film.

The use of drops containing phosphate buffer and hyaluronic acid for the therapy of the syndrome of dry eye is known (Israeli Journal of Medical Science 1997, 33, pages 194 to 197, British Journal of Opthalmology 2002, 86, pages 181-184). EP 0698388 A1 further describes an artificial lacrimal fluid, which comprises hyaluronic acid, calcium ions, citrate and phosphate ions.

Phosphates, however, disadvantageously form poorly soluble calcium phosphates with the endogenous calcium or the endogenous calcium ions or with the calcium ions contained in the pharmaceutical preparations, which can be incorporated or deposited in or on the cornea and the conjunctiva of the eye. These incorporations and/or deposits can also be designated as calcification or sclerosis and lead to a considerable impairment of the sight due to clouding of the cornea. This degeneration of the cornea is also designated as corneal ligament degeneration or band keratopathy. Even slight clouding of the cornea leads to a massively increased sensitivity to dazzle, which can be attributed to light scattering taking place on the deposits or incorporations of calcium phosphate(s). The sight in the night is thereby severely impaired. The deposition of such poorly soluble calcium phosphates or other poorly soluble calcium compounds can in particular occur on epithelial defects of the cornea and/or of the conjunctiva.

In view of the possible side effects due to calcium phosphate deposits, it would consequently be desirable to have a pharmaceutical composition which decreases and/or eliminates the abovementioned disadvantages and is suitable for topical application to the eye.

DE 101 61 110 A1 discloses a pharmaceutical composition which contains at least panthenol and/or pantothenic acid and hyaluronic acid and/or hyaluronate and optionally pharmaceutical excipients. The pharmaceutical composition disclosed in DE 101 61 110 A1 is used for the treatment of the dry eye syndrome.

DE 602 03 691 T2 discloses a dexpanthenol-containing contact lens care composition. The contact lenses treated with the dexpanthenol-containing care composition are suitable for wearing in the case of dry and/or irritated eyes.

EP 0 414 373 A2 discloses a calcium-containing and phosphate-free hyaluronate salt-containing composition for use as an isotonic and osmotically balanced salt solution during surgical operations on the eye.

U.S. Pat. No. 4,409,205 discloses an ophthalmic solution for use in the normalization of an irregularly structured tear film in mammalian eyes. The composition known from U.S. Pat. No. 4,409,205 prevents the precipitation of protein-like substances from the tears and promotes the resolubilization of deposited protein-like substances.

WO 84/04681 discloses a further ophthalmic solution for relieving the symptoms of dry eye, the composition comprising a carboxyvinyl polymer.

The object on which the invention is based is achieved by means of a pharmaceutical composition free from dexpanthenol, calcium ions and phosphate, comprising at least one calcium chelating agent and at least one opthalmologically compatible viscosity regulator, selected from the group which consists of chondroitin sulfate, polyacrylamide, polyacrylic acid, polyacrylic resins, polyethylene glycol, polysaccharides, polyvinyl-pyrrolidone, hyaluronic acid, hyaluronates, derivatives thereof and mixtures thereof, and optionally a pharmaceutical excipient or a number of pharmaceutical excipients.

Preferred refinements of the phosphate-free pharmaceutical composition according to the invention are indicated in subclaims 2 to 9.

The pharmaceutical composition according to the invention is applied topically to the surface of the eye, preferably a surface of the eye with epithelial defects in the cornea and/or conjunctiva of the eye. The epithelial defects can be caused, for example, by injury and/or operations on the eye.

A "phosphate-free pharmaceutical composition" within the meaning of the invention is understood as meaning a pharmaceutical composition which contains less than 7 mmol/l of phosphate ions, preferably less than 3 mmol/l of phosphate ions, particularly preferably less than 1 mmol/l of phosphate ions and extremely preferably no phosphate ions.

The term "phosphate ions" within the meaning of the invention is understood as meaning, in particular, $PO_4^{3-}$, $HPO_4^{2-}$ and/or $H_2PO_4^{-}$.

Viscosity regulators within the meaning of the invention are designated as substances which have a viscosity-increasing action.

Within the meaning of the invention, "opthalmologically compatible" is understood as meaning, in particular, that no irritation to the eye and preferably no adverse effects on the sight occur.

Preferably, the viscosity regulator exhibits viscoelastic behavior. Viscoelastic behavior is understood according to the invention as meaning that the viscosity changes under the action of compressive, tensile, shearing and/or shear stresses. Particularly preferably, the phosphate-free pharmaceutical composition according to the invention exhibits the behavior of a non-Newtonian liquid on account of the viscosity regulator.

The viscosity is preferably in a range from 2 to 1000 mPa·s, further preferably in a range from 2 to 500 mPa·s, particularly preferably in a range from 2 to 100 mPa·s.

The viscosity-increasing action extremely advantageously causes the phosphate-free pharmaceutical composition applied to the surface of the eye to have an increased residence time and to run off from the surface of the eye again in a retarded manner. The non-Newtonian flow behavior of the viscosity regulator calls for an outstanding characteristic for use on the eye, namely that the viscosity decreases with increasing shear rate. After application of the phosphate-free pharmaceutical composition containing the viscosity regulator to the surface of the eye, a shear stress is applied to the phosphate-free pharmaceutical composition by means of the blinking of the eyelid, whereby the initially increased viscosity is decreased. Owing to the blinking of the eyelid, the viscosity decreases such that a uniform film is formed on the surface of the eye. After blinking, the viscosity increases, such that the film adheres well to the surface of the eye and only runs off in a retarded manner.

Preferably, the viscosity regulator acts as a glidant and lubricant on the eye. The glidant and lubricant action is in particular advantageous if the surface of the eye, in particular the cornea, exhibits injuries, in particular epithelial lesions.

According to a preferred embodiment, the amount of viscosity regulator is approximately 0.005% by weight to approximately 5% by weight, preferably approximately 0.01% by weight to approximately 1% by weight, in each case based on the total weight of the phosphate-free pharmaceutical composition.

The phosphate-free pharmaceutical composition according to the invention contains, as opthalmologically compatible viscosity regulators, chondroitin sulfate, polyacrylamide, polyacrylic acid, polyacrylic resins, polyethylene glycol, cellulose derivatives, polysaccharides, polyvinylpyrrolidone, hyaluronic acid, hyaluronates, derivatives thereof and/or mixtures thereof. Particularly preferably, the opthalmologically compatible viscosity regulators used are hyaluronic acid, hyaluronates, derivatives thereof and/or mixtures thereof.

Hyaluronic acid is a constituent of the vitreous humor of the eye and inasmuch is not a foreign compound for the human body. For this reason, hyaluronic acid is very highly compatible from the immunological point of view. Moreover, hyaluronic acid or hyaluronate has a structural similarity to mucin. Mucin forms the lowermost layer of the three-layer tear film and provides for optimal wetting of the corneal and conjunctival epithelia.

Hyaluronic acid furthermore exhibits an outstanding characteristic for use on the eye, namely that the viscosity decreases with increase in the shear rate. Hyaluronic acid thus has a non-Newtonian flow behavior.

Hyaluronic acid and/or its salts, the hyaluronates and in particular sodium hyaluronate, has or have outstanding optical properties, such that no impairment of the sight occurs in the patients treated.

Hyaluronic acid or hyaluronate can be isolated from the vitreous humor of the bovine eye or else also from cockscombs. Hyaluronic acid or hyaluronates can furthermore also be produced in pharmaceutical quality in bacterial strains. Salts of hyaluronic acid which can be used are, for example, potassium, sodium and/or magnesium hyaluronate. Sodium hyaluronate is particularly preferred.

On account of these physical properties, aqueous sodium hyaluronate solutions and/or hyaluronic acid are outstandingly suitable as glidants and lubricants having a good adhesive action and prolonged residence time on the conjunctival and corneal epithelia without impairment of the sight.

According to a further embodiment, the hyaluronic acid and/or the hyaluronate has a molecular weight which is in a range from 50 000 to 10 000 000 daltons, preferably from approximately 250 000 to 5 000 000. Particularly preferably, the molecular weight of the hyaluronic acid or of the hyaluronate is 50 000 to 4 000 000 daltons. Extremely preferably, the hyaluronic acid or hyaluronate has a molecular weight of approximately 1 500 000 to 3 500 000 daltons. The hyaluronic acid and/or the hyaluronate are preferably used in a concentration of from 0.01 to 1.0% by weight, furthermore preferably from 0.05 to 0.8% by weight, particularly preferably from 0.08 to 0.4% by weight, in each case based on the total weight of the phosphate-free pharmaceutical composition.

The high molecular weight of the hyaluronic acid or of the hyaluronate used such as, for example, sodium hyaluronate causes a high viscoelasticity at low concentration. The molecular chains are present in the solution in a tangled random arrangement. Under the influence of the shear forces exerted by the movement of the eyelid, the macromolecules align approximately parallel. This change in the three-dimensional structure under the influence of shear forces is probably important for the outstanding viscoelastic properties.

Calcium chelating agents within the meaning of the invention are preferably understood as meaning substances which prevent precipitation of calcium salts by complexing and/or binding the Ca ions.

Preferably, the calcium chelating agent of the phosphate-free pharmaceutical composition according to the invention is selected from the group which consists of citrate salts, citric acid, EDTA (ethylene-diaminetetraacetic acid), EGTA (ethylene glycol bis(2-aminoethyl)-N,N,N',N'-tetraacetic acid) and mixtures thereof.

Particularly preferably, the phosphate-free pharmaceutical composition according to the invention comprises a citrate buffer. The use of citrate buffer is particularly advantageous, since the citrate buffer on the one hand acts as a buffer system and on the other hand as a calcium chelating agent, whereby the addition of further buffer system is no longer imperatively necessary.

In one embodiment, the phosphate-free pharmaceutical composition according to the invention comprises 0.04 to 0.06 mg/ml of citric acid and 7.5 to 9.5 mg/ml of trisodium citrate dihydrate, the pH of the pharmaceutical composition according to the invention preferably being 6.6 to 7.8.

For the preparation of the citrate buffer, both citric acid and primary, secondary and/or tertiary citrates can be used. The citrates used are preferably alkali metal citrates, furthermore preferably sodium citrate. Preferably, citric acid, sodium citrate, disodium citrate and/or trisodium citrate are used.

In one embodiment, the calcium chelating agent is present in the phosphate-free pharmaceutical composition according to the invention in a concentration of from 0.05 to 10% by weight, furthermore preferably from 0.1 to 5% by weight, particularly preferably from 0.5 to 3% by weight, in each case based on the total weight of the pharmaceutical composition. In a further embodiment, the calcium chelating agent is present in the phosphate-free pharmaceutical composition according to the invention in a concentration of from 0.8 to 1.0% by weight, in each case based on the total weight of the pharmaceutical composition.

The phosphate-free pharmaceutical composition itself is calcium ion-free. Calcium ion-free within the meaning of the invention means that the phosphate-free pharmaceutical composition contains less than 0.3 mmol/l of calcium ions, preferably less than 0.1 mmol/l of calcium ions and particularly preferably no calcium ions.

On account of the absence of phosphate ions and on account of the presence of at least one calcium chelating agent, the pharmaceutical composition according to the invention prevents the formation of calcium phosphate complexes and/or calcium phosphate compounds and/or other poorly soluble Ca compounds in the eye, which can lead to deposits or incorporations on or in the cornea and consequently to a considerable restriction of the sight due to light scattering by the calcium phosphate complexes and/or calcium phosphate compounds and/or other poorly soluble Ca compounds. Poorly soluble calcium compounds are preferably understood as meaning compounds which form deposits or incorporations in the cornea.

The calcium chelating agent complexes physiologically present calcium ions and consequently counteracts the formation of poorly soluble calcium compounds, in particular of calcium phosphate compounds, which can lead to deposits or incorporations in the cornea and/or conjunctiva of the eye.

The pharmaceutical composition according to the invention prevents or decreases calcification in the cornea and/or in the conjunctiva. Moreover, it is possible by means of the phosphate-free composition according to the invention to dissolve calcium phosphate complexes and/or calcium phosphate compounds and/or other poorly soluble calcium compounds preferably also already deposited from and/or out of the cornea.

The outstanding glidant and lubricant properties of hyaluronic acid or hyaluronate interact synergistically with the calcium chelating agent, which prevents the deposition and/or incorporation of calcium-containing compounds or complexes in the cornea, in the eye treated with the phosphate-free pharmaceutical composition according to the invention and make possible the provision of an unusually highly compatible wetting solution.

Surprisingly, it has also been found that the viscosity of hyaluronic acid-containing solutions and/or hyaluronate-containing solutions which contain no phosphate ions is higher than that of solutions with an identical amount of hyaluronic acid and/or hyaluronate which contain phosphate ions. Advantageously, lower concentrations of hyaluronic acid or hyaluronate can thus be employed in the phosphate-free composition according to the invention in order to achieve a long-lasting wetting of the eye. Since hyaluronic acid or hyaluronate is very expensive in pharmaceutical quality, considerable costs can be saved.

Preferably, the phosphate-free pharmaceutical composition is provided in preservative-free form. Preservatives can damage the precorneal film and lead to a reduction in the number of the microvilli and microplicae of the superficial corneal epithelial cells. Thus long-term therapy with opthalmological pharmaceutical compositions which contain preservatives can lead to epithelial damage on its own. In particular, the widespread benzalkonium chloride has a great damage potential. In view of the desired therapy of the eye, irritation by the addition of a preservative is therefore to be avoided. Furthermore, preservatives prevent the regeneration of the ocular epithelia and are therefore to be avoided in the treatment of already damaged eyes, e.g. in the sicca syndrome, or after traumas, e.g. after surgical interventions.

In one embodiment, the pharmaceutical composition according to the invention comprises no panthenol, pantothenic acid, heparin, moxaverin and/or their salts.

The term panthenol or pantothenic acid is furthermore also to be understood as meaning their derivatives. Panthenol can be present, for example, as dexpanthenol. Pantothenic acid is also to be understood as meaning its salts the pantothenates, for example sodium pantothenate.

The term "heparin" is to be understood as meaning "mucopolysaccharides having heparin activity". A "mucopolysaccharide having heparin activity" is preferably to be understood as meaning any mucopolysaccharide or glucosaminoglycan which has a biological or physiological activity comparable to heparin. The mucopolysaccharide having heparin activity is selected, for example, from the group which consists of heparinoids, human heparin, animal heparin, recombinant heparin, chemically modified heparin, enzymatically modified heparin, truncated heparin, low molecular weight heparin, heparan sulfate and mixtures thereof.

According to a preferred embodiment, the aforementioned medicaments panthenol, in particular dexpanthenol, pantothenic acid, heparin, moxaverin and/or their salts are not contained in the phosphate-free pharmaceutical composition according to the invention.

It has completely surprisingly turned out that a phosphate-free composition which contains no panthenol, in particular no dexpanthenol, is very suitable for the treatment of epithelial defects in the cornea and/or conjunctiva of the eye. Although the active substance panthenol, in particular dexpanthenol, is extensively used in the healing of wounds, it has completely inexplicably turned out that in the case of injuries of the cornea and/or conjunctiva of the eye, very good healing occurs if the phosphate-free pharmaceutical composition contains no panthenol, in particular no dexpanthenol. Thus the present invention makes possible the provision of a pharmaceutical composition comprising only a few components and having an outstanding activity profile. The composition according to the invention can consequently be produced more cost-effectively, since the active substance dexpanthenol can be dispensed with out, however, having a poorer healing action.

When using the phosphate-free pharmaceutical composition according to the invention, incorporation and/or deposition of poorly soluble calcium compounds such as calcium phosphate compounds furthermore does not occur. When using conventional phosphate buffer-containing ocular preparations, on the other hand, incorporations and/or deposits, in particular of calcium phosphate compounds, also occur in the healing cornea and/or conjunctiva of the eye.

The present invention thus represents a great advance, since when using the composition according to the invention these incorporations and/or deposits in and/or on the cornea and/or conjunctiva of the eye are reliably avoided and at the same time a very good healing of cornea and/or conjunctiva of the eye is obtained.

According to a preferred embodiment, the phosphate-free pharmaceutical composition consists of at least one calcium chelating agent and at least one opthalmologically compatible viscosity regulator and optionally a pharmaceutical excipient or a number of pharmaceutical excipients. In this case, "of at least one" means that the phosphate-free pharmaceutical composition consists of one or more calcium chelating agents and of one or more opthalmologically compatible viscosity regulators and optionally of one or more pharmaceutical excipients.

According to a particularly preferred embodiment, the phosphate-free pharmaceutical composition consists of citric acid and/or citrate salts and hyaluronate and/or hyaluronic acid and optionally a pharmaceutical excipient or a number of pharmaceutical excipients.

In one embodiment, the pharmaceutical composition according to the invention comprises no further pharmaceutical in addition to the calcium chelating agent, hyaluronic acid and/or hyaluronates. Pharmaceuticals within the meaning of the invention are in particular to be understood as meaning substances which in the living body cause the prevention, healing and/or alleviation of diseases.

Preferably, for the storage and release of a preservative-free pharmaceutical composition according to the invention the COMOD® system described in "PTA today" 1996, No. 12, page 1230 to 1232 is used, which allows sterile storage and repeated release of the phosphate-free pharmaceutical composition according to the invention. Of course, conventional single-dose containers can also be used, which are discarded after use.

In one embodiment, the phosphate-free pharmaceutical composition can comprise further pharmaceutical excipients which are opthalmologically compatible. The pharmaceutical excipients here are preferably free from phosphate ions.

Preferably, the pharmaceutical excipients are selected from the group which consists of inorganic buffer substances, organic buffer substances, inorganic salts, organic salts, viscosity regulators, solvents, solubilizers, solution accelerators, salt-forming agents, salts, viscosity- and consistency-influencing agents, gel-forming agents, emulsifiers, solubilizers, wetting agents, spreading agents, antioxidants, preservatives, fillers and carriers, osmolarity regulators and mixtures thereof.

It is further preferred that the phosphate-free pharmaceutical composition is present in the form of a solution, suspension or emulsion, of a gel, of an ointment or paste, or of a powder, granules or a tablet. The phosphate-free pharmaceutical composition is preferably an ophthalmic agent, furthermore preferably an ophthalmic agent for topical application.

In the case of the provision of the phosphate-free pharmaceutical composition in the form of eye ointments or eye gels, this is provided, for example, in petroleum jelly or paraffin with and without addition of emulsifier such as, for example, cholesterol, wool wax, wool wax alcohols, cetanol etc.

According to a preferred embodiment, the phosphate-free pharmaceutical composition is present in the form of a solution, such that this can be applied to the surface of the eye, for example, in the form of eyedrops or of an eye spray.

In one embodiment, the osmolarity of the phosphate-free pharmaceutical composition according to the invention is 100 to 900 mOsm/l.

The preferably aqueous solutions in this case, according to a preferred embodiment, are isotonic solutions, based on the tear fluid. In isotonic solutions the osmolarity is preferably 200 to 350 mOsm/l, preferably 300 mOsm/l. According to a further preferred embodiment, the phosphate-free pharmaceutical composition according to the invention is hypoosmolar. In this case, the osmolarity can be, for example, approximately 160-180 mOsm/l. A hypoosmolar solution is used, in particular, if an abnormally high osmolarity of a tear film has to be compensated in a patient with dry eyes. Depending on the syndrome to be treated, a hypertonic solution can also be advantageous. The pharmaceutical composition can in this case also have a particularly high osmolarity of 700 to 900 mOsm/l.

For the isotonicization of the aqueous solution, sodium chloride, boric acid, sorbitol, glycerol, etc. are preferably used.

The pH of the aqueous solution is preferably in a range from pH 5 to 9, furthermore preferably in a range from pH 6.8 to 7.6, particularly preferably in a range from pH 7.2 to 7.4. For the adjustment of the pH, buffer solutions such as, for example, acetate buffer, acetate/borate buffer and borate buffer can be used. According to the invention, however, no phosphate buffers are used.

Of course, it is possible that the phosphate-free pharmaceutical composition according to the invention is present in the form of a solid, which before application is first dissolved in an aqueous solution such as, for example, a buffer solution. After the dissolution of a solid, for example in an aqueous buffer solution, the solution can be sterile filtered and can then be applied to the surface of the eye as an eye spray or eyedrops. Preferably, solid and solvent are already present in sterile form in the case of separate storage, such that sterile filtration after the preparation of the solution is not necessary. The user can thus directly apply the phosphate-free pharmaceutical composition after preparation of the mixture or solution.

In the case of provision of a phosphate-free pharmaceutical composition in the form of a solid such as, for example, of a powder, granules or a tablet, the phosphate-free pharmaceutical composition preferably comprises sodium citrate and/or citric acid and hyaluronic acid and/or sodium hyaluronate, since these compounds are very highly soluble in water.

Fundamentally, the phosphate-free pharmaceutical composition according to the invention can also be introduced into the conjunctival sac in the form of eye tablets. The eye tablet rapidly dissolves under the action of tear fluid.

Preferably, however, the application of the phosphate-free pharmaceutical composition takes place in the form of eyedrops, eye sprays and/or eye gels.

Before the application of the solution or of the solid, the compounds are mixed with one another in the desired quantitative ratios and dissolved and subsequently sterile filtered with addition of water or aqueous buffer solutions.

The object on which the invention is based is furthermore achieved by use of at least one opthalmologically compatible viscosity regulator and at least one calcium chelating agent for the production of a phosphate-free pharmaceutical composition for the treatment and/or prevention of epithelial defects in the cornea and/or conjunctiva.

According to the invention, the phosphate-free pharmaceutical composition is used in one embodiment for the treatment and/or prevention of the calcification or of clouding of the ligamentous cornea. The calcification in particular occurs on epithelial defects, which can have different causes.

For example, the epithelial defects are selected from the group consisting of epithelial defects produced by mechanical and/or chemical actions, epithelial defects after surgical interventions, epithelial defects due to wetting disorders of the surface of the eye or epithelial defects due to long-term treatment with preservative-containing pharmaceutical compositions or with contact lenses. Epithelial defects, for example cuts, chemical burns and lesions, make possible the incorporation and/or deposition of poorly soluble calcium compounds, in particular of calcium phosphates, into and/or on cornea of the eye.

For example, the wetting disorders are selected from the group consisting of Sjögren syndrome, sicca syndrome and wetting disorders in contact lens wearers. Wetting disorders in the eye lead to increased abrasion in the eye or on the surface of the eye. Merely as a result of this abrasion, epithelial defects can occur which significantly increase the risk of calcification.

The epithelial defects caused by mechanical actions can be, for example, accident-related injuries.

The epithelial defects caused by chemical actions can result, for example, due to chemical burns with acids and/or alkalis.

In one embodiment, the surgical interventions are selected from the group consisting of surgical interventions in the anterior section of the eye, cataract extraction with lens implantation, refractive-surgical interventions, interventions on the cornea and corneal transplants.

In one embodiment, the opthalmological phosphate-free pharmaceutical composition according to the invention is employed in long-term treatment, in particular of chronic diseases in the eye. In particular, the opthalmological phosphate-free pharmaceutical composition according to the invention is employed in the long-term treatment of allergies and/or glaucoma. Long-term treatment within the meaning of the invention is understood as meaning a treatment of preferably more than one year, particularly preferably of more than one month, extremely preferably of more than one week.

Preferably, in the use according to the invention the phosphate-free composition is calcium-free and/or dexpanthenol-free.

According to a further preferred embodiment, in the use according to the invention the viscosity regulator is selected from the group which consists of chondroitin sulfate, polyacrylamide, polyacrylic acid, polyacrylic resins, polyethylene glycol, cellulose derivatives, polysaccharides, polyvinyl alcohol, polyvinylpyrrolidone, hyaluronic acid, hyaluronates, derivatives thereof and mixtures thereof.

The phosphate-free pharmaceutical composition can furthermore be used as artificial tears, for example for rewetting in the case of contact lens wearers.

Incidentally, with respect to the use according to the invention reference is made to the above embodiments for the composition according to the invention, which correspondingly also apply in the case of the use according to the invention.

EXAMPLES

Example 1

| 1 ml of eyedrops contains: | |
|---|---|
| sodium hyaluronate (MW: $1.5 \times 10^6 - 3.5 \; 10^6$ Da) | 1.0 mg |
| sorbitol | 32.0 mg |
| citric acid, anhydrous | 0.05 mg |
| sodium citrate × 2 H$_2$O | 8.5 mg |
| water for injection to | 1.0 ml |
| pH 6.8 to 7.6 | |

Example 2

| | |
|---|---|
| sodium hyaluronate (MW: $1.5 \times 10^6 - 3.5 \; 10^6$ Da) | 5.0 mg |
| citric acid, anhydrous | 29.5 mg |
| sodium citrate × 2 H$_2$O | 500 mg |
| water for injection | to 50 ml |
| pH 6.25 | |
| 109 mOsm/kg | |

Example 3

| | |
|---|---|
| sodium hyaluronate (MW: $1.5 \times 10^6 - 3.5 \; 10^6$ Da) | 10.0 mg |
| citric acid, anhydrous | 0.3 mg |
| sodium citrate × 2 H$_2$O | 50 mg |
| glycerol, anhydrous | 2500 mg |
| water for injection | to 100 ml |
| pH 7.11 | |
| 270 mOsm/kg | |

The sodium citrate employed according to Example 1 to 3 is a trisodium citrate dihydrate of pharmacopoeia quality. The compositions according to Example 1 to 3 can contain further constituents for isotonicization and for isohydration.

Example 4

In this example, the healing action of eyedrops was compared with one another taking into consideration sclerosis and calcification phenomena in the cornea of phosphate-containing eyedrops and phosphate-free eyedrops according to the invention.

The phosphate-containing eyedrops used for comparison in this case had the following composition:

| | |
|---|---|
| sodium hyaluronate (MW: $1.5 \times 10^6 - 3.5 \times 10^6$ Da) | 1 mg |
| sorbitol | 27 mg |
| phosphate buffer pH 7.2 | 50 mM |
| water for injection purposes | to 1 ml |

The phosphate-free eyedrops according to the invention in this case had the following composition:

| | |
|---|---|
| sodium hyaluronate (MW: $1.5 \times 10^6 - 3.5 \times 10^6$ Da) | 1 mg |
| sorbitol | 32 mg |
| citric acid, anhydrous | 0.05 mg |
| sodium citrate × 2 H$_2$O | 8.5 mg |
| water for injection | to 1 ml |
| pH 7.2 | |

The healing action taking into consideration sclerosis or calcification phenomena in the cornea of the eye was investigated on corneas which were removed from rabbits freshly killed with carbon dioxide gas after taking out the eyes. After removing the retina, choroidea, lens and iris, the corneas with residues of the sclera were fixed in a holding device in a culture chamber. The anterior chamber of the eye lying behind the cornea was then carefully filled with culture medium in the culture chamber.

The culture medium used was Earle's MEM T031-05 from Biochrom, Berlin, Germany. The pH of the culture medium was adjusted to pH 7.2 with addition of NaHCO$_3$.

The culture medium was continuously exchanged under continuous flow with a flow rate of 10 µl/minute. The average volume of the artificial anterior chamber was 0.5 to 0.9 ml, depending on the curvature of the cornea. An exchange of culture medium consequently took place over a period of 50 to 90 minutes.

The corneas were cultured under sterile conditions at 32° C. under 100% atmospheric humidity in an incubator.

In order to investigate the healing action taking into consideration calcification phenomena on the corneas, the corneal surface was injured in the form of four small erosions each having an area of about 0.2 to 1.5 mm$^2$ using a dentist's grinder (Arkansas grinder 638XF, Meisinger, Germany).

Above the corneal apex, a drip cannula was arranged such that it dripped centrally onto the cornea. Using a micropump, one drop of liquid with a volume of in each case about 30 µl of the culture medium, the phosphate-containing eyedrops or the phosphate-free eyedrops was applied per hour.

The eyedrops of culture medium served as a control for the comparison of the corneas treated with the phosphate-containing or phosphate-free eyedrops.

In order to be able to investigate the calcification phenomena in the cornea, a calcium chloride-containing saline solution having a CaCl$_2$ concentration of 14.58 mmol/l was further dripped onto the corneas at one drop (30 μl)/h. The dripping on of the calcium chloride-containing physiological salt solution served for the simulation of tear secretion. The concentration of free calcium ions corresponds here to the calcium content in the secreted tear fluid.

The dripping on of eyedrops or calcium chloride solution took place alternately, in each case at 30 minute intervals.

The corneas investigated were completely viable in the tests. The viability was measured by means of the pH and the glucose and lactate concentration in the medium of the culture chambers. All values were constant over the measurement period.

The measurement period was in each case 4 days.

The result with respect to the calcification and healing of the corneas is summarized in Table 1.

TABLE 1

Result of calcification and healing

| Run no. | Cornea no. | Type of exposure | Severity of the calcification | Calcification occurred (≥1) | Healing [%] |
|---|---|---|---|---|---|
| 1 | HH1 | medium | 1 | yes | 49.7 |
| 1 | HH2 | phosphate-free | 0 | no | 89.8 |
| 1 | HH3 | phosphate-containing | 4 | yes | 22 |
| 2 | HH7 | medium | 4 | yes | 97.8 |
| 2 | HH8 | phosphate-free | 0 | no | 100 |
| 2 | HH9 | phosphate-containing | 3 | yes | 92 |
| 3 | HH13 | medium | 3 | yes | n.d. |
| 3 | HH16 | phosphate-free | 4 | yes | n.d. |
| 3 | HH17 | phosphate-containing | 0 | no | 94.8 |

Explanation of the table:
1 n.d.: not determined.
2 The details of the healing in % indicates the size of the healed area relative to the original area of the corneal injury.
3 The strength of the calcification was indicated by means of the value numbers 1 to 5, the assessment taking place with the naked eye and the value numbers standing for the following assessments:
0: no sclerotic phenomena
1: first scleroses are discernible with the naked eye
2: slight sclerosis
3: medium severe sclerosis
4: severe sclerosis
5: complete sclerosis

BRIEF DESCRIPTION OF THE DRAWINGS

The invention now will be described with respect to the drawings, wherein:

Photomicrographs of treated and untreated corneas are shown under transmitted light observation in FIGS. 1 to 9. The corneas of rabbit eyes kept and mounted and also treated under culture conditions are in each case to be seen.

Figure 1:
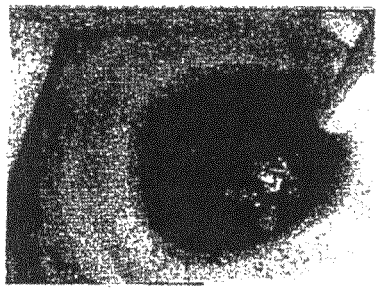

It is shown in FIG. 1 how the corneal injury is applied using a dentist's grinder.

Figure 2:
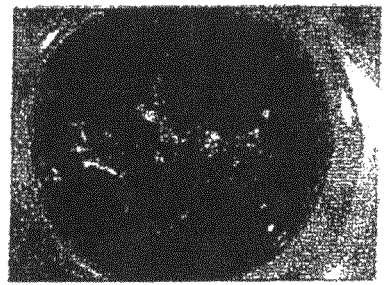

The injuries to the corneal surface, also designated as abrasion, are shown in FIG. 2.

Figure 3:
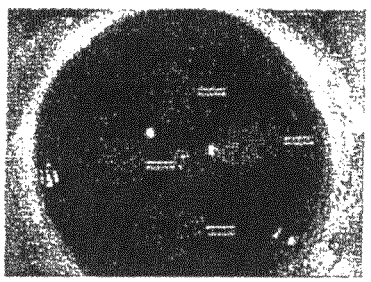

The injuries inflicted on the cornea of the eye are rendered better visible in FIG. 3 with staining by fluorescein.

Figure 4:
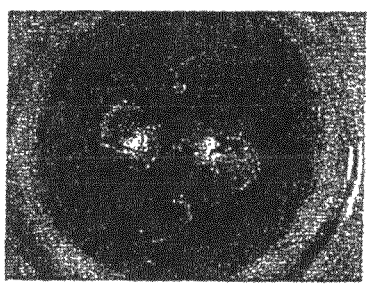

The injured cornea at the beginning of the experiment with the phosphate-free eyedrops from Example 4 is shown in FIG. 4.

Figure 5:

The cornea from FIG. 4 after dripping on phosphate-free eyedrops for 4 days is shown in FIG. 5. It is evident from FIG. 5 that no calcification of the corneal surface at all occurred after dripping on the phosphate-free eyedrops for 4 days.

Figure 6:
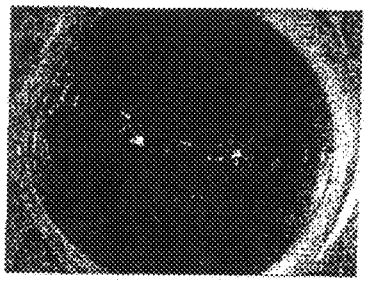

The cornea at the beginning of the experiment with the phosphate-containing eyedrops from Example 4 is shown in FIG. 6.

Figure 7:
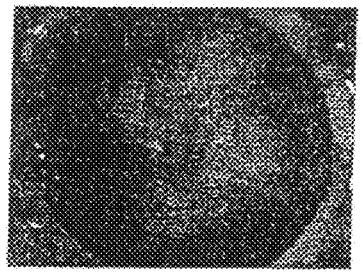

The cornea from FIG. 6 after dripping on the phosphate-containing eyedrops is shown after 4 days in FIG. 7. It is evident from FIG. 7 that severe calcification of the corneal surface occurred after dripping on the phosphate-containing eyedrops for 4 days.

Figure 8:
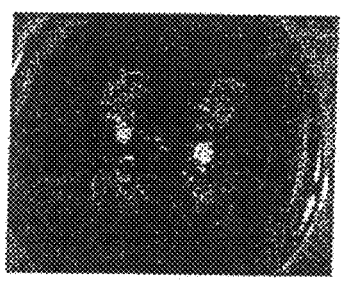

The cornea at the beginning of the control experiment with culture medium, as described in Example 4, is shown in FIG. 8.

Figure 9:
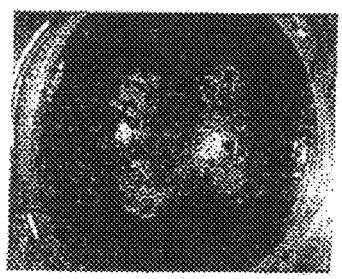

The corneal surface from FIG. 8 after dripping on the culture medium for 4 days can be seen in FIG. 9. As is evident from FIG. 9, a medium severe to severe calcification of the corneal surface occurred after dripping on culture medium for 4 days.

Result:

It has completely surprisingly been shown that on treatment of epithelial defects in the cornea and/or conjunctiva of the eye with phosphate-free eyedrops which contain a calcium chelating agent, no calcification of the corneal surface occurs, i.e. in particular no incorporation of calcium phosphate compounds.

Further, it has surprisingly turned out that the phosphate-free pharmaceutical composition according to the invention, even in the absence of dexpanthenol, which is customarily used to a wide extent for wound healing, brings about very good healing of an injured cornea of the eye.

It is evident from Table 1 that the healing rates averaged over the two or three experimental courses were 73.8% in the case of culture medium, 57% in the case of the phosphate-containing eyedrops and 94.9% in the case of the phosphate-free eyedrops.

Unlike the treatment with the phosphate-containing eyedrops, in which a severe calcification of the corneal surface occurred with an average assessment number of approximately 4, it was not possible to determine any calcification of the corneal surface in the case of the use of phosphate-free eyedrops.

The invention claimed is:

1. A method of treating epithelial defects in the cornea and/or conjunctiva of the eye, comprising:
    administering to an animal a pharmaceutical composition, said pharmaceutical composition consisting of a liquid and being free of phosphates, moxaverin, heparn, panthenol and/or pantothenic acid, and wherein the concentration of calcium ions in said composition is less than 0.1 mmol/l, and said pharmaceutical composition includes at least one calcium chelating agent selected from the group consisting of citrate salts, citric acid, and mixtures thereof, and at least one ophthalmologically compatible viscosity regulator selected from the group consisting of hyaluronic acid, hyaluronates, and mixtures thereof, wherein said hyaluronic acid, or hyaluronate, has a molecular weight of from about 50,000 to about 10,000,000 Daltons, in amounts effective to treat said epithelial defects in the cornea and/or conjunctiva of the eye, wherein said epithelial defects in the cornea and/or conjunctiva of the eye result from wetting disorders of the surface of the eye and are selected from the group consisting of Sjögren syndrome, sicca syndrome, and wetting disorders of the eye in contact lens wearers.

2. The method of claim 1 wherein said phosphate-free pharmaceutical composition is employed for application for a period of more than one week.

3. The method of claim 1 wherein incorporations and/or deposits of poorly soluble calcium compounds in the cornea and/or conjunctiva of the eye are prevented and/or reduced.

4. The method of claim 1, wherein said pharmaceutical composition is free of calcium ions.

5. The method of claim 1, wherein said viscosity regulator is present in said pharmaceutical composition in an amount of from about 0.005% by weight to about 5% by weight.

6. The method of claim 5, wherein said viscosity regulator is present in said pharmaceutical composition in an amount of from about 0.01% by weight to about 1% by weight.

7. The method of claim 1 wherein said hyaluronic acid, or hyaluronate, has a molecular weight of from about 250,000 to about 5,000,000 Daltons.

8. The method of claim 1 wherein said hyaluronic acid, or hyaluronate, is sodium hyaluronate.

9. The method of claim 1, wherein said pharmaceutical composition further comprises at least one pharmaceutical excipient.

10. The method of claim 9, wherein said at least one pharmaceutical excipient is selected from the group consisting of inorganic buffer substances, organic buffer substances, inorganic salts, organic salts, solvents, solubilizers, solution accelerators, salt-forming agents, emulsifiers, solubilizers, wetting agents, spreading agents, antioxidants, preservatives, fillers and carriers, osmolarity regulators, and mixtures thereof.

11. The method of claim 1, wherein said pharmaceutical composition is in the form of a solution, of drops, of a spray, or of a suspension or emulsion.

12. The method of claim 1, wherein said pharmaceutical composition is free of preservatives.

\* \* \* \* \*